US010956806B2

(12) United States Patent
Masuda et al.

(10) Patent No.: US 10,956,806 B2
(45) Date of Patent: Mar. 23, 2021

(54) EFFICIENT ASSEMBLY OF OLIGONUCLEOTIDES FOR NUCLEIC ACID BASED DATA STORAGE

(71) Applicant: INTERNATIONAL BUSINESS MACHINES CORPORATION, Armonk, NY (US)

(72) Inventors: Koji Masuda, Tokyo (JP); Eiji Nakamura, Kawasaki (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/436,043

(22) Filed: Jun. 10, 2019

(65) Prior Publication Data
US 2020/0387769 A1 Dec. 10, 2020

(51) Int. Cl.
*G11C 11/00* (2006.01)
*G11C 13/00* (2006.01)
*G06N 3/00* (2006.01)
*C07H 21/04* (2006.01)
*C12Q 1/6853* (2018.01)
*G16B 30/20* (2019.01)

(52) U.S. Cl.
CPC ............ *G06N 3/002* (2013.01); *C07H 21/04* (2013.01); *C12Q 1/6853* (2013.01); *G16B 30/20* (2019.02)

(58) Field of Classification Search
CPC ........ G06N 3/123; G16B 30/20; G11C 11/00; C12Q 1/6853
See application file for complete search history.

(56) References Cited

U.S. PATENT DOCUMENTS

| 2003/0022150 A1* | 1/2003 | Sampson | C12Q 1/6837 506/7 |
| 2004/0166498 A1* | 8/2004 | Peterson | G16B 30/00 435/6.12 |
| 2018/0088112 A1* | 3/2018 | Fan | C12Q 1/6869 |
| 2018/0121478 A1* | 5/2018 | Walder | G16B 30/00 |
| 2018/0253563 A1* | 9/2018 | Peck | H04L 9/3231 |
| 2019/0244109 A1* | 8/2019 | Bramlett | C12N 15/1068 |

(Continued)

FOREIGN PATENT DOCUMENTS

| CN | 106845158 A | 6/2017 |
| WO | 2017190297 A1 | 11/2017 |

(Continued)

OTHER PUBLICATIONS

Allentoft, "The Half-life of DNA in Bone: Measuring Decay Kinetics in 158 Dated Fossils", Proceedings of the Royal Society B, Oct. 2012, 11 pages.

(Continued)

*Primary Examiner* — Toan K Le
(74) *Attorney, Agent, or Firm* — Tutunjian & Bitetto, P.C.; Randall Bluestone

(57) ABSTRACT

A computer-implemented method for efficient assembly of oligonucleotides for nucleic acid based data storage includes receiving encoded data including binary data encoded into nucleic acid sequence data, and assembling a target nucleic acid data strand based on the encoded data by, concatenating one or more selected codeword oligonucleotides obtained from a codeword stack strand.

20 Claims, 10 Drawing Sheets

Specification includes a Sequence Listing.

(56) References Cited

U.S. PATENT DOCUMENTS

2019/0271032 A1* 9/2019 Owen .................. C12Q 1/6848
2019/0390178 A1* 12/2019 Champion ....... C12Y 207/0703

FOREIGN PATENT DOCUMENTS

WO      2018102064 A1     6/2018
WO      2018148260 A1     8/2018

OTHER PUBLICATIONS

Blawat, "Forward Error Correction for DNA Data Storage", Procedia Computer Science, vol. 80, Jun. 2016, pp. 1101-1022.

Bornholt, "A DNA-Based Archival Storage System", ASPLOS, Apr. 2016, pp. 637-649.

Church, "Next-Generation Digital Information Storage in DNA", Science Mag, vol. 337, Sep. 2012, pp. 1628.

Erlich, "DNA Fountain Enables a Robust and Efficient Storage Architecture", Science Magazine, vol. 355, Issue 6328, Mar. 2017, pp. 950-954.

Goldman, "Towards Practical, High-Capacity, Low-Maintenance Information Storage in Synthesized DNA", Nature, vol. 494, Feb. 2013, pp. 77-80.

Grass, "Robust Chemical Preservation of Digital Information on DNA in Silica with Error-Correcting Codes", Angew Chem Int Ed, Feb. 2015, 5 pages.

Kim, "Shotgun DNA Synthesis for the High-Throughout Construction of Large DNA Molecule", Nucleic Acids Research, Jun. 2012, 8 pages.

Kosuri, "Scalable Gene Synthesis by Selective Amplification of DNA Pools from High-Fidelity Microchips", Nature Biotechnology, vol. 28, No. 12, Dec. 2010, pp. 1295-1301.

Kosuri, "Large-Scale de novo DNA Synthesis: Technologies and Applications", Nature Method, vol. 11, No. 5, May 2014, pp. 499-507.

Organick, "Randsom Access in Large-Scale DNA Data Storage", Nature Biotechnology, Feb. 2018, 13 pages.

Quan, "Parallel On-Chip Gene Synthesis and Application Optimization of Protein Expression", Nature Biotechnology, vol. 29, No. 5, May 2011, pp. 449-453.

Schwartz, "Accurate Gene Synthesis with Tag-Directed Retrieval of Sequence-Verified DNA Molecules", Nature Methods, vol. 9, No. 9, Sep. 2012, pp. 913-917.

Service, "DNA Could Store All the World's Data in One Room", Science Mag, Mar. 2017, 8 pages.

http://catalog.takaro-bio.co.jp/com/tech_info_detail.php?mode+1&masterid=M100000511#4, Mar. 2019, 9 pages.

* cited by examiner

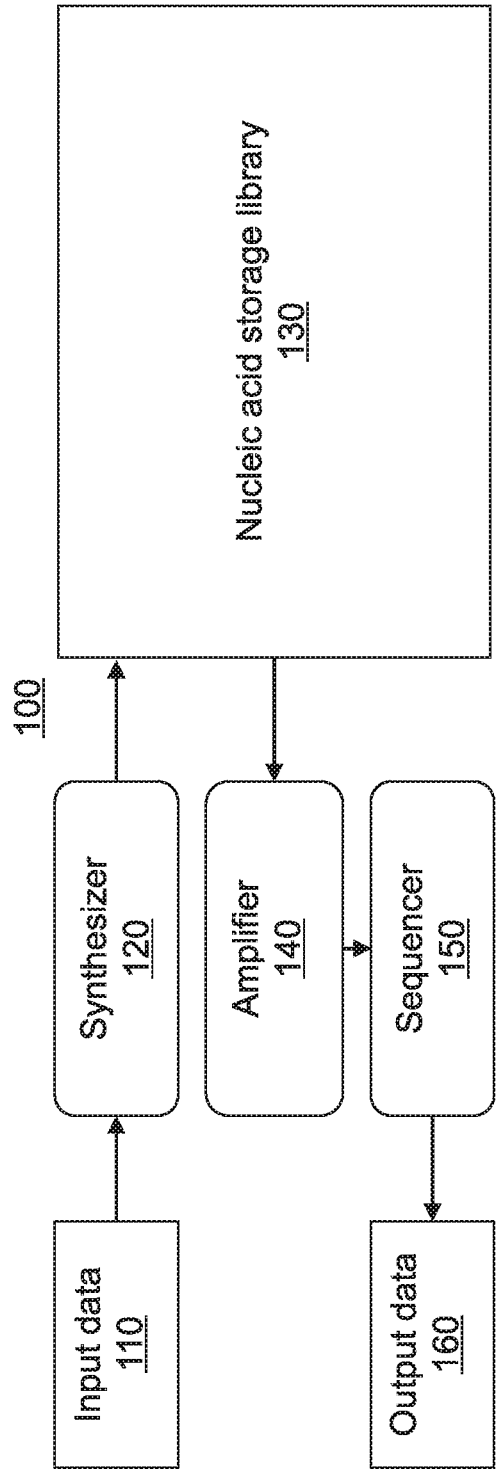
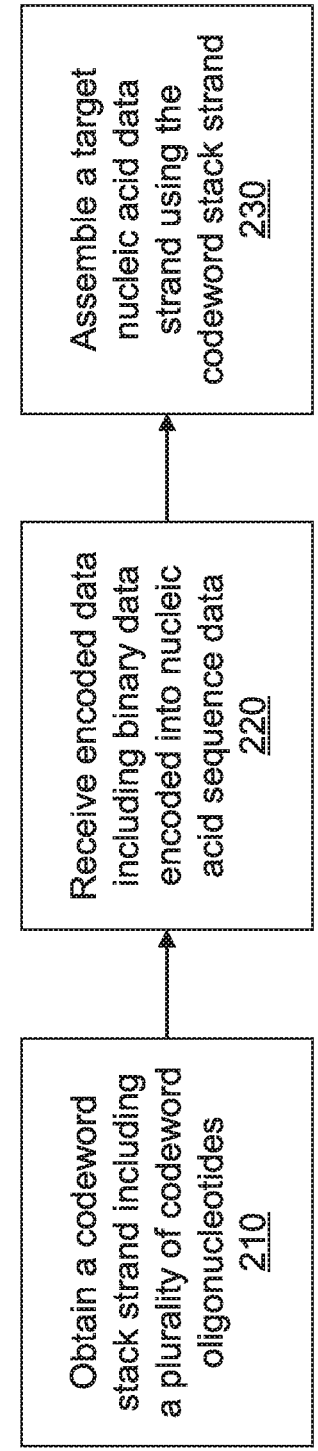

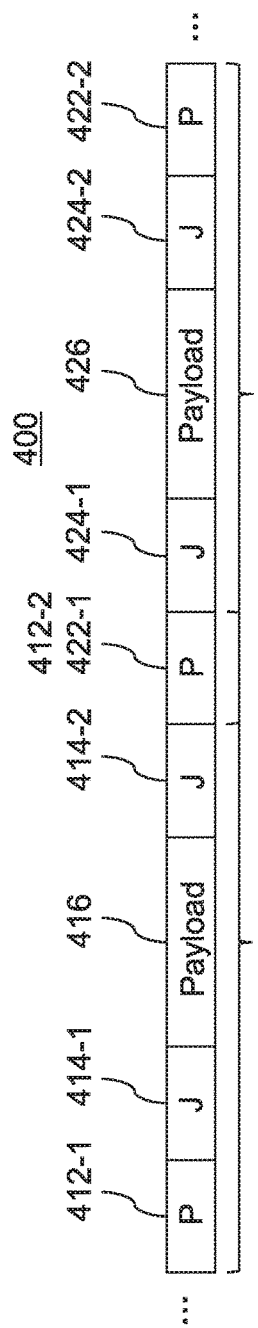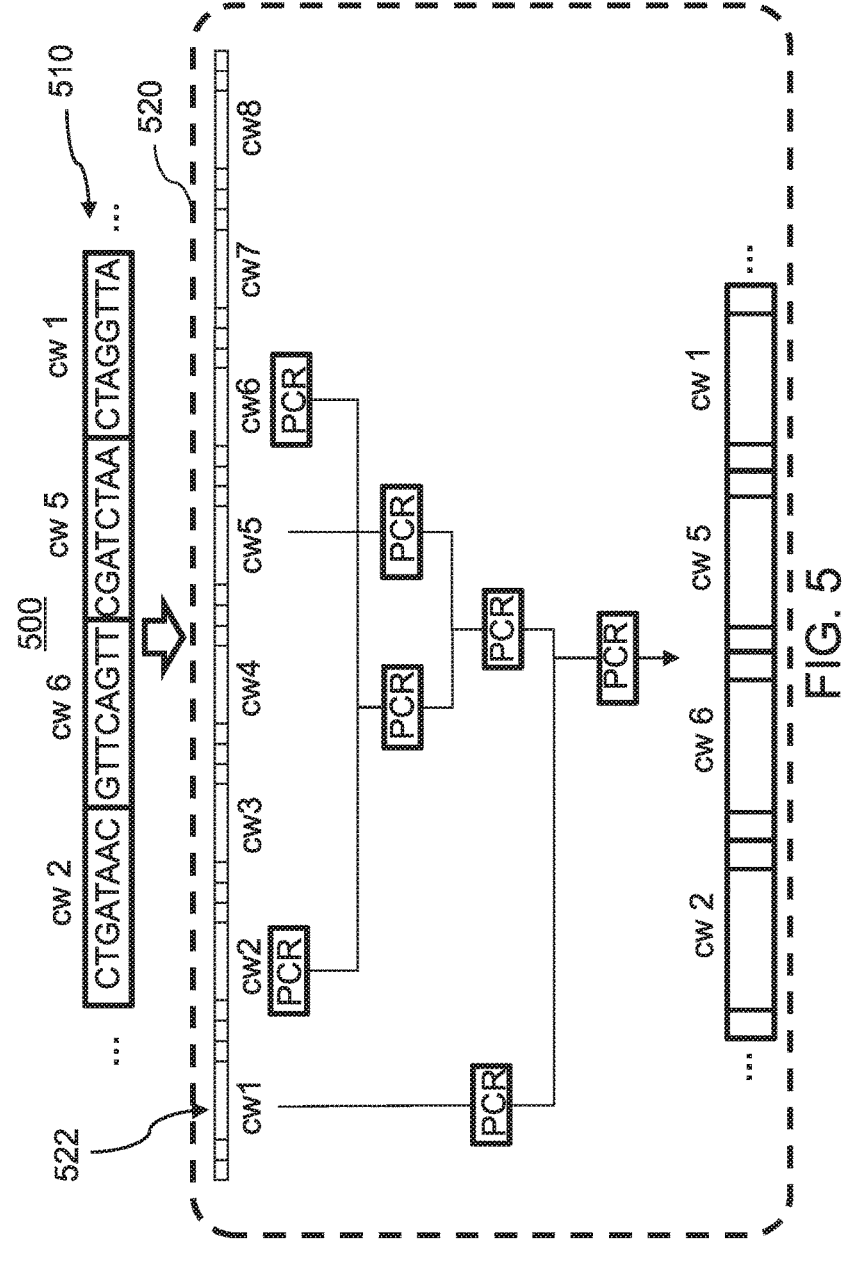

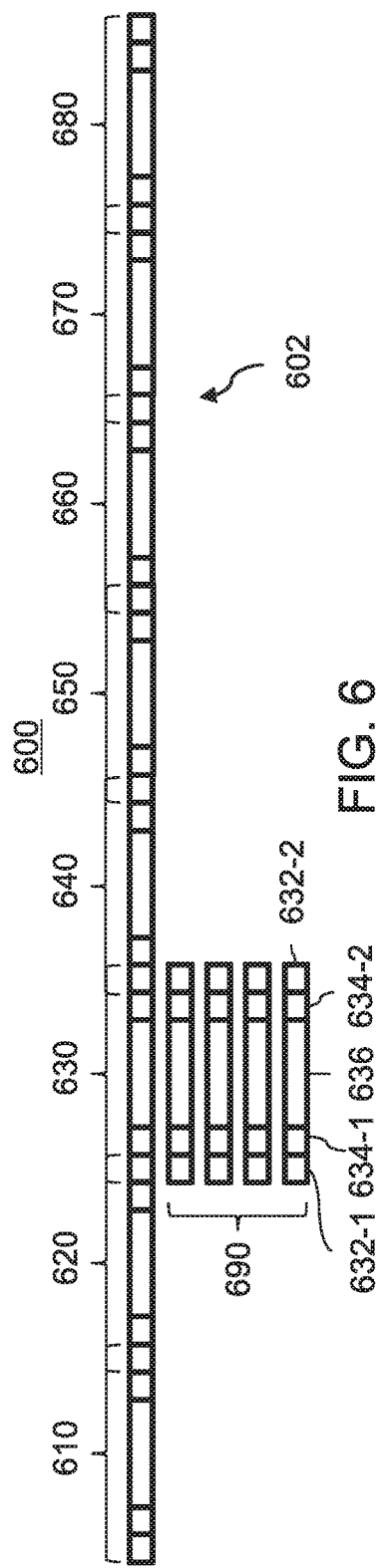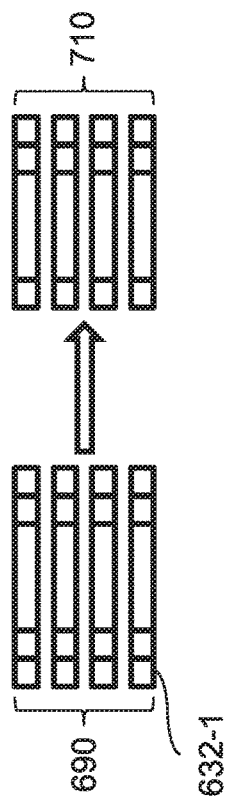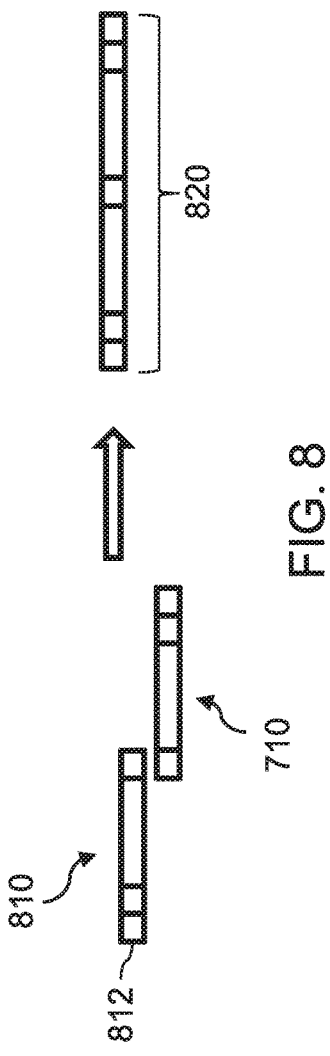

```
1600
├─ 1610 ─┤
AGTTAGGATCCACGGGCGCTCCGTTA  AAGGCCTCTTAAGCAACACCTCCTC
TCAATCCTAGGTGCCGCGAGGCAAT   TTCCGGAGAATTCGTTGTGGAGGAG

├─ 1620 ─┤
AGTTAGGATCCACGGGCGCTCCGTTA  AAGGCCTCTTAAGCAACACCTCCTC
TCAATCCTAGGTGCCGCGAGGCAAT   TTCCGGAGAATTCGTTGTGGAGGAG
```

FIG. 16

SEQUENCE LISTING

<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Randomly generated sequence for exemplary
      purposes

<400> SEQUENCE: 1
agcccatcga                                                          10

<210> SEQ ID NO 2
<211> LENGTH: 25
<212> TYPE: DNA

-continued

```
<213> ORGANISM: Artificial Sequence
<220> FEATURE:
<223> OTHER INFORMATION: Randomly generated sequence for exemplary
      purposes

<400> SEQUENCE: 2
agttaggatc cacggcgctc cgtta                                           25

<210> SEQ ID NO 3
<211> LENGTH: 25
<212> TYPE: DNA
<213> ORGANISM: Artificial Sequence
<220> FEATURE:
<223> OTHER INFORMATION: Randomly generated sequence for exemplary
      purposes

<400> SEQUENCE: 3
tcaatcctag gtgccgcgag gcaat                                           25

<210> SEQ ID NO 4
<211> LENGTH: 25
<212> TYPE: DNA
<213> ORGANISM: Artificial Sequence
<220> FEATURE:
<223> OTHER INFORMATION: Randomly generated sequence for exemplary
      purposes

<400> SEQUENCE: 4
aaggcctctt aagcaacacc tcctc                                           25

<210> SEQ ID NO 5
<211> LENGTH: 25
<212> TYPE: DNA
<213> ORGANISM: Artificial Sequence
<220> FEATURE:
<223> OTHER INFORMATION: Randomly generated sequence for exemplary
      purposes

<400> SEQUENCE: 5
ttccggagaa ttcgttgtgg aggag                                           25
```

EFFICIENT ASSEMBLY OF OLIGONUCLEOTIDES FOR NUCLEIC ACID BASED DATA STORAGE

INCORPORATION BY REFERENCE OF A SEQUENCE LISTING

The application includes references to nucleic acid sequences which have been submitted concurrently herewith via EFS-Web as the Sequence Listing text file "P201806337US01_SeqListing", generated via PatentIn version 3.5 on Dec. 13, 2019, having a size of 2 KB, and hereby incorporated by reference herein in its entirety.

BACKGROUND

The present invention generally relates to data storage systems, and more particularly to nucleic acid based data storage.

Due to high packing density and chemical stability, nucleic acid molecules such as, e.g., deoxyribonucleic acid (DNA) molecules, can be used as long-term data storage media. For example, DNA molecules can preserve their chemical structures in a natural environment for long durations of time due to long half-lives (e.g., multiple centuries).

SUMMARY

In accordance with an embodiment of the present invention, a system for efficient assembly of oligonucleotides for nucleic acid based data storage is provided. The system includes a memory device for storing program code and at least one processor device operatively coupled to the memory device. The at least one processor device is configured to execute program code stored on the memory device to receive encoded data including binary data encoded into nucleic acid sequence data, and assemble a target nucleic acid data strand based on the encoded data by concatenating one or more selected codeword oligonucleotides obtained from a codeword stack strand.

In accordance with another embodiment of the present invention, a computer-implemented method for efficient assembly of oligonucleotides for nucleic acid based data storage is provided. The method includes receiving encoded data including binary data encoded into nucleic acid sequence data, and assembling a target nucleic acid data strand based on the encoded data by concatenating one or more selected codeword oligonucleotides obtained from a codeword stack strand.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 1 is a block diagram of a nucleic acid data processing system, in accordance with an embodiment of the present invention;

FIG. 2 is a block/flow diagram of a system/method for efficient assembly of oligonucleotides for nucleic acid based data storage, in accordance with an embodiment of the present invention;

FIG. 4 is a diagram of an exemplary codeword stack strand for polymerase chain reaction (PCR) assembly, in accordance with an embodiment of the present invention;

FIG. 5 is a diagram of an overview of the assembly of a target nucleic acid strand, in accordance with an embodiment of the present invention;

FIG. 6 is a diagram of the amplification of a codeword oligonucleotide selected from a codeword stack strand, in accordance with an embodiment of the present invention;

FIG. 7 is a diagram of the cleaving of a first primer site sequence from the codeword oligonucleotide of FIG. 6, in accordance with an embodiment of the present invention;

FIG. 8 is a diagram of the concatenation of a header oligonucleotide with the codeword oligonucleotide of FIG. 7 to form a target sequence, in accordance with an embodiment of the present invention;

FIG. 16 is a diagram of an elongation step performed for GG assembly after the annealing step, in accordance with an embodiment of the present invention;

DETAILED DESCRIPTION

Figure 3:
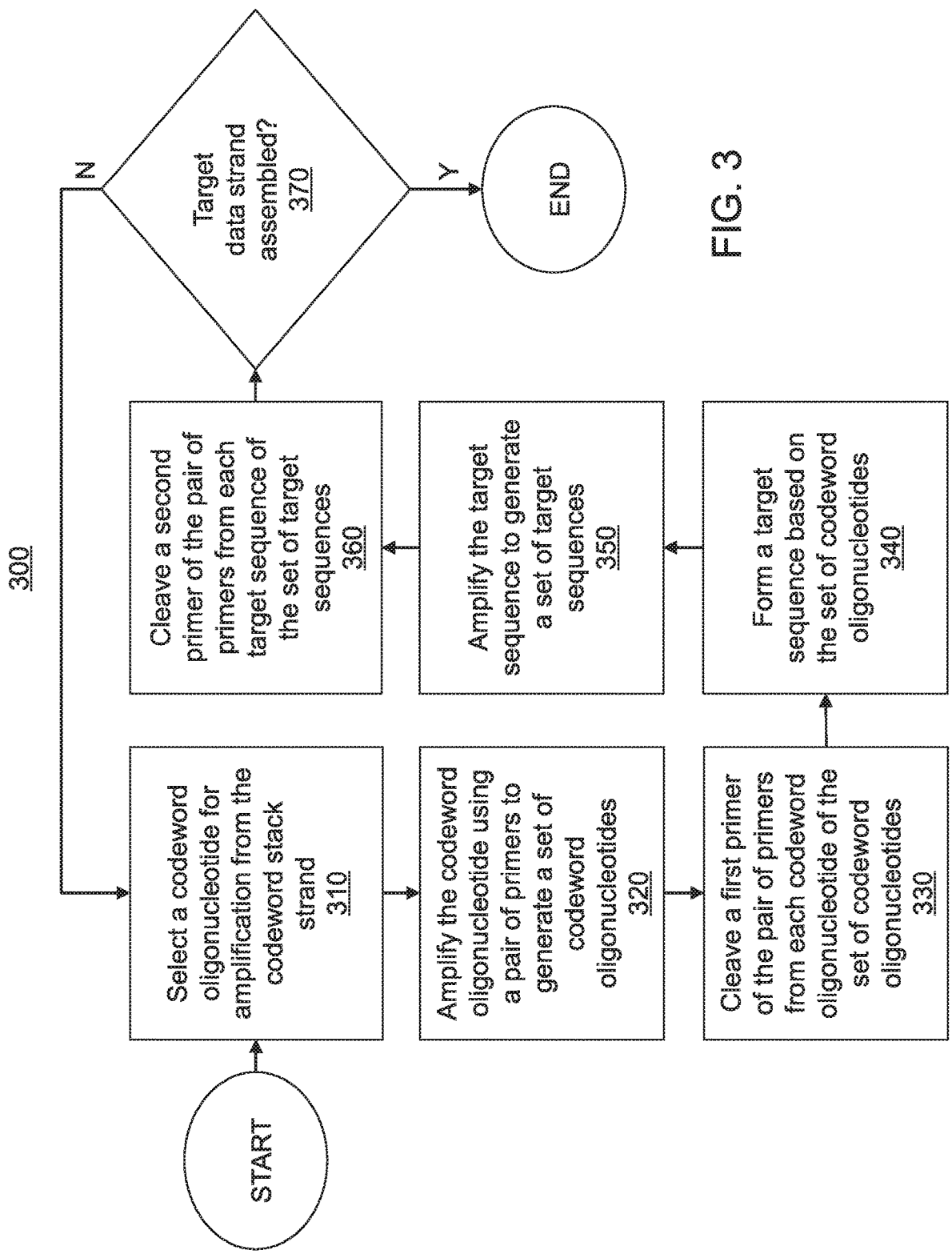
FIG. 3 is a block/flow diagram of a system/method for assembling a target nucleic acid strand based on a codeword stack strand, in accordance with an embodiment of the present invention.

The embodiments described herein can be used to efficiently assembly of oligonucleotides for nucleic acid data storage, thereby increasing speed and decreasing costs of synthesizing nucleic acid strands (e.g., DNA strands). The costs can be incurred to the chemical operations and agents needed to synthesize the oligonucleotides for nucleic acid data storage.

For example, data can be encoded into blocks of finite numbers of codewords with redundancy for error-correction. For nucleic acid data based storage in accordance with the embodiments described herein, codewords of a set of codewords can be mapped into short sequences of nucleotides to generate codeword oligonucleotides representing the codewords. Since the members of the set of codewords can be defined arbitrarily, the embodiments described herein can assemble a nucleic acid data strand representing data more efficiently based on the codeword oligonucleotides. The nucleic acid data strand can be assembled by concatenating the codeword oligonucleotides without having to synthesize new oligonucleotides to construct an arbitrary data strand.

More specifically, the embodiments described herein can initially synthesize a "codeword stack" of nucleic acid strands by oligonucleotide synthesis, use the codeword stack as a mold to generate codeword oligonucleotides (e.g., by polymerase chain reaction (PCR), golden gate assembly (GG), or other suitable technique), and concatenate the codeword oligonucleotides in an arbitrary order to construct the nucleic acid data strand. Accordingly, since the codeword oligonucleotide generation can be performed after the initial synthesis of the codeword stack, cost and time can be reduced for assembling the nucleic acid data strand.

The embodiments described herein can be implemented in a variety of methods. For example, the embodiments described herein can be implemented using an inkjet-based method. As another example, the embodiments described herein can be implemented using a microfluidics-based method.

Referring now to the drawings in which like numerals represent the same or similar elements and initially to FIG. 1, a block diagram is provided illustrating an exemplary nucleic acid data processing system 100. In an illustrative embodiment, the system 100 can be configured to process deoxyribonucleic acid (DNA) data. However, the system 100 can be configured to process any suitable nucleic acid data in accordance with the embodiments described herein (e.g., ribonucleic acid (RNA) data).

As shown, input data 110 can be provided to a synthesizer 120. The input data 110 can include encoded binary data. More specifically, the input data 110 can include binary data encoded into nucleic acid sequence data (e.g., DNA sequence). The synthesizer 120 can perform nucleic acid synthesis to generate nucleic acid segments based on the input data 110. Any suitable process can be used to implement the synthesizer 120 in accordance with the embodiments described herein.

The synthesizer 120 can output the nucleic acid segments to a nucleic acid storage library 130 for storage (a "write"). For example, the nucleic acid storage library 130 can include a DNA storage library.

The synthesizer 120 and/or the storage library 130 can output a nucleic acid sequence to an amplifier 140, also referred to herein as a thermal cycler or thermocycler, to amplify the nucleic acid sequence. The amplification is performed to obtain a desired number of copies of the nucleic acid sequence. Any suitable amplifier technology can be used to amplify nucleic acid segments in accordance with the embodiments described herein.

Illustratively, the amplifier 140 can amplify the nucleic acid sequence via polymerase chain reaction (PCR). In PCR, a target sequence can be amplified after n cycles to obtain a desired number of copies of the target sequence. More specifically, in a first cycle, the target sequence can be denatured using a denaturation process employed at a high temperature. For example, the temperature can be selected within a range of, e.g., about 95° C. to about 100° C. Then, primers of the denatured target sequence can be selectively annealed. The annealing can be performed at a temperature selected within a range of, e.g., about 50° C. to about 65° C. After the primers of the denatured target sequence are selectively annealed, a strand extension is performed. The strand extension can be performed using polymerase at a temperature of about, e.g., 72° C. The denaturation, anneal and extension processes can repeat for n–1 more cycles to achieve sufficient amplification. For example, the target sequence can be amplified to, e.g., $10^5$-$10^6$ after, e.g., 25-30 cycles.

The amplifier 140 can provide a nucleic acid sequence as a sample to a sequencer 150. The sequencer 150 is configured to automate nucleic acid sequencing (e.g., DNA sequencing) based on the sample. More specifically, the sequencer 150 is configured to determine an order of nucleobases (which can also be referred to as nitrogenous bases or bases) based on the sample. The sequencer 150 can then generate output data 160 (a "read"). The output data 160 can include a text string representing the order of the bases determined by the sequencer 150. Any suitable sequencing technology can be used to perform nucleic acid sequencing in accordance with the embodiments described herein.

The system 100 can be configured to implement efficient assembly of oligonucleotides for nucleic acid based data storage in accordance with the embodiments described herein, as will be now be described in further detail with reference to FIG. 2.

With reference to FIG. 2, a block/flow diagram is provided illustrating a system/method 200 for efficient assembly of oligonucleotides for nucleic acid based data storage. As will be described in further detail below, the system/method 200 can assemble a target nucleic acid data strand by consecutive amplifications and contiguous concatenation of oligonucleotides representing codewords, without having to chemically synthesize the oligonucleotides from scratch. The system/method 200 can be implemented using an inkjet-based method, a microfluidics-based method, etc.

Generally, error correction can be performed on segments of data. Redundant bits can be added to information bits, constituting a codeword. Data can then be encoded with a finite set of codewords of an error-correcting code. For example, assume that "01010100" corresponds to a segment of binary data. Redundancy can be added to the segment of binary data "01010100" to form a codeword. For example, a codeword that can be formed from the segment of binary data "01010100" can be "0101010011011000", where "11011000" is the added redundancy. Metadata can optionally be added to the codeword. For example, an index "0010" can be added to the codeword to form modified codeword "00100101010011011000". Bit-to-sequence mapping can be performed to map the (modified) codeword to a nucleic acid sequence.

For example, bases corresponding to DNA include adenine ("A"), guanine ("G"), cytosine ("C") and thymine ("T"). Bit pairs (e.g., "00", "10", "01" and "11") can be mapped to respective ones of the bases. Illustratively, if "00" maps to "A", "10" maps to "G", "01" maps to "C" and "11" maps to "T", then modified codeword "00100101010011011000" can be mapped to a sequence corresponding to SEQ ID NO:1. In the event that the bases correspond to another nucleic acid, other bases can be used. For example, T can be replaced by uracil ("U") if the nucleic acid is RNA.

With this in mind, at block 210, a codeword stack strand including a plurality of codeword oligonucleotides is obtained. An oligonucleotide generally refers to a nucleic acid molecule formed from a small number of nucleotides (e.g., a short nucleic acid molecule). Each of the codeword nucleotides corresponds to a codeword. The codeword stack strand functions as a base structure or "mold" for amplifying or copying codeword oligonucleotides to form a target nucleic acid data strand. The codeword stack strand can be synthesized chemically using, e.g., phosphoramidite chemistry.

The codeword stack strand can include all or partial sets of codeword oligonucleotides concatenated in series using oligonucleotide synthesis. More specifically, each codeword oligonucleotide of the codeword stack strand can include a payload sequence corresponding to the codeword sandwiched between two primer site sequences, or pair of primers, and two joint site sequences, or pair of joint sites. The primer site sequences can include unique and non-interacting nucleotide "primer" sequences (e.g., 20-25 nucleotide sequences), while the joint site sequences can include, e.g., 15-20 nucleotide sequences. The primer site sequences are unique identifiers for the codeword oligonucleotide. Codewords can be joined by annealing the joint site sequences. The joint site sequences can be orthogonal joint site sequences, which, as will be described in further detail below, can allow for multi-parallel assembly of multiple data strands. An illustrative example of codeword stack strands will be described below with reference to FIGS. 4 and 13.

At block 220, encoded data including binary data encoded into nucleic acid sequence data is received. For example, the nucleic acid sequence data can include e.g., DNA sequence data. The binary data can be encoded using error-correcting codes. Examples of error-correcting codes that can be used in accordance with the embodiments described herein include, but are not limited to, repetitive codes, parity check codes, Hamming codes, Bose-Chaudhuri-Hocquenghem (BCH) codes, Reed-Solomon codes, fountain codes, etc.

At block 230, a target nucleic acid data strand is assembled using the codework stack strand. More specifically, the target nucleic acid data strand can be assembled using codeword oligonucleotides selected from the codeword stack strand. The nucleic acid data strand can be assembled using any suitable technique in accordance with the embodiments described herein.

For example, in one embodiment, the nucleic acid data strand can be assembled using a PCR assembly technique. In another embodiment, the nucleic acid data strand can be assembled using a GG assembly technique. Further details regarding the assembly of the target nucleic acid data strand using a PCR assembly technique are described below with reference to FIGS. 3-11, and further details regarding the assembly of the target nucleic acid data strand using a GG assembly technique are described below with reference to FIGS. 12-17.

With reference to FIG. 3, a block/flow diagram is provided illustrating a system/method 300 for assembling a target nucleic acid data strand. The system/method 300 can be used to assemble a target nucleic acid data strand, as described above with reference to FIG. 2. For example, in one embodiment, the system/method 300 can use a PCR assembly technique to assemble the target nucleic acid data strand, as will be described in further detail below with reference to FIGS. 4-11. In another embodiment, the system/method 300 can use a GG assembly technique to assemble the target nucleic acid data strand, as will be described in further detail below with reference to FIGS. 12-17.

At block 310, a codeword oligonucleotide is selected for amplification from a codeword stack strand. The codework stack strand can be synthesized by chemical synthesis (e.g., phosphoramidite synthesis). An illustrative example of a codeword stack strand that can be used within the context of PCR assembly will be described below with reference to FIG. 4, and an illustrative example of a codeword stack strand that can be used within the context of GG assembly will be described below with reference to FIG. 12.

At block 320 the codeword oligonucleotide is amplified using a pair of primers to generate a set of codeword oligonucleotides. The codeword oligonucleotide can be arbitrarily selected from the codeword stack strand. The pair of primers can include orthogonal primers. The pair of primers sandwich the payload sequence of the codeword oligonucleotide. Any suitable amplification technique(s) can be used to amplify the codeword oligonucleotide in accordance with the embodiments described herein.

At block 330, a first primer of the pair of primers is cleaved from each codeword oligonucleotide of the set of oligonucleotides. For example, the first primer can be a left primer. The first primer can be cleaved by using restriction enzymes. Fragments produced by the restriction enzymes can be joined by complementary base-pairing.

At block 340, a target sequence is formed based on the set of codeword oligonucleotides. In one embodiment, forming the target sequence includes concatenating at least two sequences including the codeword oligonucleotide. For example, a header oligonucleotide can be concatenated with the codeword oligonucleotide. The header oligonucleotide can be located at the beginning of the target nucleic acid data strand for use an identifier of the target nucleic acid data strand and a primer site for amplification during a strand extension process. The header oligonucleotide can further include a joint site to enable a directed elongation of the target nucleic acid data strand. The any suitable technique can be used to form the target sequence in accordance with the embodiments described herein (e.g., PCR assembly).

At block 350, the target sequence is amplified to generate a set of target sequences. Any suitable process can be used to amplify the target sequence in accordance with the embodiments described herein (e.g., PCR).

At block 360, a second primer of the pair of primers is cleaved from each target sequence of the set of target sequences. The cleaving can generate a plurality of subsequences from the set of target sequences. For example, if the first primer is the left primer, the second primer can be a right primer. The second primer can be cleaved using restriction enzymes. Fragments produced by the restriction enzymes can be joined by complementary base-pairing.

The following table provides a non-exhaustive list of restriction enzymes that can be used to perform the cleaving at blocks 330 and 360, including corresponding recognition sequences and cuts:

TABLE 1

| Enzyme | Recognition Sequence | Cut |
|---|---|---|
| AluI | 5'AGCT | 5'-AG CT-3' |
|  | 3'TCGA | 3'-TC GA-5' |
| BamHI | 5'GGATCC | 5'-G GATCC-3' |
|  | 3'CCTAGG | 3'-CCTAG G-5' |
| ClaI | 5'ATCGAT | 5'-AT CGAT-3' |
|  | 3'TAGCTA | 3'-TAGC TA-5' |
| EcoRI | 5'GAATTC | 5'-G AATTC-3' |
|  | 3'CTTAAG | 3'-CTTAA G-5' |
| EcoRV | 5'GATATC | 5'-GAT ATC-3' |
|  | 3'CTATAG | 3'-CTA TAG-5' |
| HaeIII | 5'GGCC | 5'-GG CC-3' |
|  | 3'CCGG | 3'-CC GG-5' |
| HindIII | 5'AAGCTT | 5'-A AGCTT-3' |
|  | 3'TTCGAA | 3'-TTCGA A-5' |

TABLE 1-continued

| Enzyme | Recognition Sequence | Cut |
|---|---|---|
| HinfI | 5'GANTC | 5'-G ANTC-3' |
|  | 3'CTNAG | 3'-CTNA G-5' |
| HpaI | 5'GTTAAC | 5'-GTT AAC-3' |
|  | 3'CAATTG | 3'-CAA TTG-5' |
| HpaII | 5'CCGG | 5'-C CGG-3' |
|  | 3'GGCC | 3'-GGC C-5' |
| KpnI | 5'GGTACC | 5'-GGTAC C-3' |
|  | 3'CCATGG | 3'-C CATGG-5' |
| NotI | 5'GCGGCCGC | 5'-GC GGCCGC-3' |
|  | 3'CGCCGGCG | 3'-CGCCGG CG-5' |
| PovII | 5'CAGCTG | 5'-CAG CTG-3' |
|  | 3'GTCGAC | 3'-GTC GAC-5' |
| PstI | 5'CTGCAG | 5'-CTGCA G-3' |
|  | 3'GACGTC | 3'-G ACGTC-5' |
| SacI | 5'GAGCTC | 5'-GAGCT C-3' |
|  | 3'CTCGAG | 3'-C TCGAG-5' |
| SalI | 5'GTCGAC | 5'-G TCGAC-3' |
|  | 3'CAGCTG | 3'-CAGCT G-5' |

At block 370, it is determined whether a target nucleic acid data strand has been assembled. For example, it is determined whether the plurality of subsequences correspond to the target nucleic acid data strand. If yes, this means that the target nucleic acid data strand has been assembled and the process terminates. If the target nucleic acid data strand has yet to be assembled, the process reverts back to block 310 to select a next codeword oligonucleotide from the codeword stack strand for amplification to assemble the target nucleic acid data strand by concatenating the next codeword oligonucleotide with the plurality of subsequences.

FIGS. 4-11 will now describe the assembly of a target nucleic acid data strand using PCR assembly.

With reference to FIG. 4, an exemplary codeword stack strand 400 for PCR assembly implementation is provided. The codeword stack strand 400 includes a plurality of codeword oligonucleotides, including codeword oligonucleotide 410 and codeword oligonucleotide 420.

Although only two codeword oligonucleotides 410 and 420 are shown, the codeword stack strand 400 can include any number of codeword oligonucleotides. Accordingly, the codework stack strand 400 depicted in FIG. 4 should not be considered limiting.

As shown, the codeword oligonucleotide 410 includes a first primer site sequence 412-1, a first joint site sequence 414-1, a payload sequence 416, a second joint site sequence 414-2 and a second primer site sequence 412-2. That is, the codeword oligonucleotide 410 includes a payload sequence 416 sandwiched between primer site sequences 412-1 and 412-2, and joint site sequences 414-1 and 414-2.

The codeword oligonucleotide 420 includes a first primer site sequence 422-1 (which is the same as the second primer site sequence 412-2), a first joint site sequence 424-1, a payload sequence 426, a second joint site sequence 424-2 and a second primer site sequence 422-2. That is, the codeword oligonucleotide 420 includes a payload sequence 426 sandwiched between primer site sequences 422-1 and 422-2, and joint site sequences 424-1 and 424-2. Accordingly, the codeword stack strand 400 includes codewords design for PCR assembly.

In this PCR assembly case, recognitions sites for restriction enzymes can be embedded jointly over the junction of the primer and joint sites. In a GG assembly case, as will be described in further detail below with reference to FIG. 13, recognition sites for restriction enzymes can be independently inserted between primer and joint sites.

With reference to FIG. 5, a diagram 500 is provided illustrating efficient assembly of oligonucleotides for nucleic acid based data storage using a PCR assembly technique. As shown, encoded sequence data 510 is provided to assembly component 520 as a target nucleic acid data strand. The encoded sequence data 510 includes codeword ("cw") 2 corresponding to the sequence CTGATAAC, cw 6 corresponding to the sequence GTTCAGTT, cw 5 corresponding to the sequence CGATCTAA, and cw 1 corresponding to the sequence CTAGGTTA.

In assembly component 520, a codeword stack strand 522 includes eight codeword oligonucleotides having respective payload sequences corresponding to respective codewords. As shown, the codework stack strand 522 includes payload sequences corresponding to codewords cw1 through cw8. The target nucleic acid data strand is assembled by selecting respective ones of the codewords of the codeword stack strand 522 for amplification and assembly (e.g., using PCR).

An illustrative example of an assembly of a target nucleic acid data strand in accordance with the embodiments described herein will now be described below with reference to FIGS. 6-11.

With reference to FIG. 6, a diagram 600 is provided illustrating a codeword stack strand 602 including a plurality of codeword oligonucleotides 610 through 680. Diagram 600 illustrates an exemplary implementation of blocks 310 and 320 described above with reference to FIG. 3.

As shown, codeword oligonucleotide 630 includes a first primer site sequence 632-1, a first joint site sequence 634-1, a payload sequence 636, a second joint site sequence 634-2 and a second primer site sequence 632-2. In this illustrative example, the codeword oligonucleotide 630 has been selected for amplification and amplified to generate a set of codeword oligonucleotides 690. Although the set 690 is shown including four copies of the codeword oligonucleotide 630 in this illustrative example, such a number should not be considered limiting.

With reference to FIG. 7, a diagram 700 is provided showing the cleaving of the first primer site 632-1 from each codeword oligonucleotide of the set 690 to generate a plurality of modified codeword oligonucleotides 710. Diagram 700 illustrates an exemplary implementation of block 330 described above with reference to FIG. 3.

With reference to FIG. 8, a diagram 800 is provided showing the concatenation of a header oligonucleotide including a header sequence 812 with a modified codeword oligonucleotide 710 to generate a target sequence 820. Diagram 800 illustrates an exemplary implementation of block 340 described above with reference to FIG. 3.

Figure 9:
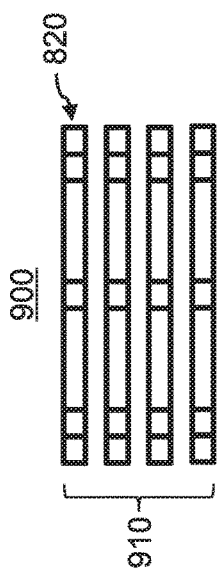
FIG. 9 is a diagram of the amplification of the concatenated oligonucleotide of FIG. 8, in accordance with an embodiment of the present invention.

With reference to FIG. 9, a diagram 900 is provided showing the amplification of the target sequence 820 to generate a set of target sequences 910. Although the set 910 is shown including four copies of the codeword target sequence 820 in this illustrative example, such a number should not be considered limiting. Diagram 900 illustrates an exemplary implementation of block 350 described above with reference to FIG. 3.

Figure 10:
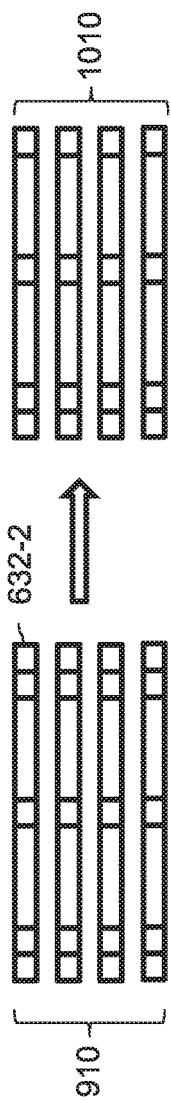
FIG. 10 is a diagram of the cleaving of a second primer sequence associated with the codeword oligonucleotide from the concatenated oligonucleotide of FIG. 9, in accordance with an embodiment of the present invention.

With reference to FIG. 10, a diagram 1000 is provided showing the cleaving of the second primer site 632-2 from each target sequence of the set 910 to generate a plurality of first sequences 1010. Diagram 1000 illustrates an exemplary implementation of block 360 described above with reference to FIG. 3.

Figure 11:
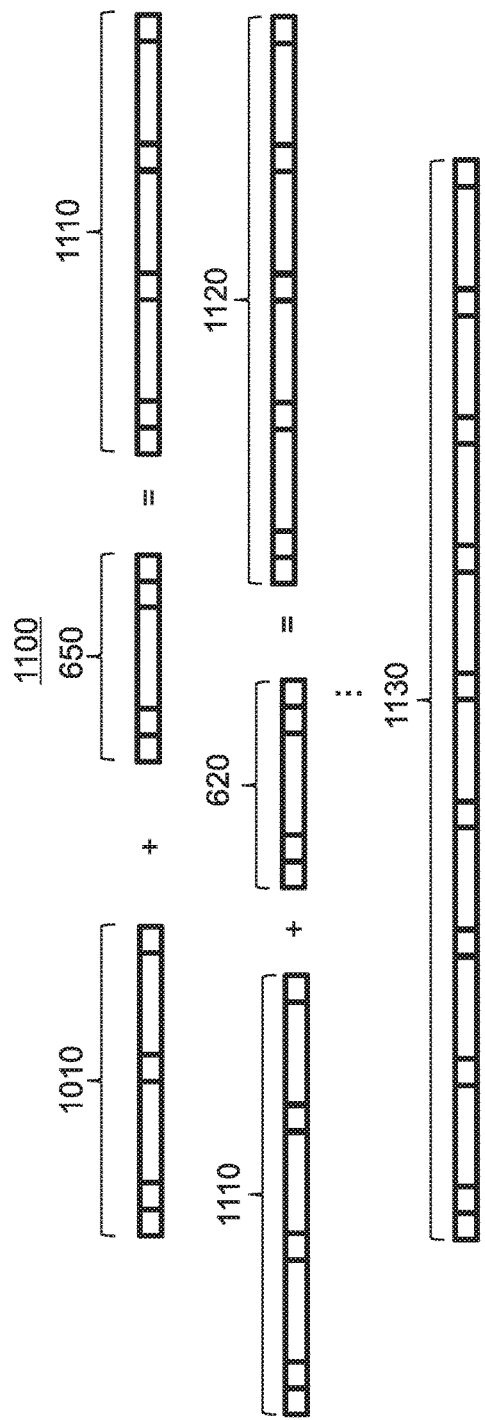
FIG. 11 is a diagram of the assembly of a target nucleic acid data strand based on the concatenated oligonucleotide of FIG. 10, in accordance with an embodiment of the present invention.

With reference to FIG. 11, a diagram 1100 is provided showing the selection of another codeword oligonucleotide 650 for amplification and concatenation with a first sequence 1010 to generate a second sequence 1110 in a manner similar to what has been described with reference to FIGS. 6-10. Then, another codeword oligonucleotide 620 is selected for amplification and concatenation with the second sequence 1110 to generate a third sequence 1120. The amplification and concatenation process continues until a target nucleic acid data strand 1130 is obtained. Diagram 1000 illustrates an exemplary implementation of block 370 described above with reference to FIG. 3.

FIGS. 4-11 describe embodiments for oligonucleotide synthesis using PCR assembly. In an alternative embodiment, and as mentioned above, oligonucleotide synthesis can be performed using GG assembly methods. Further details regarding oligonucleotide synthesis using GG assembly will now be described below with reference to FIGS. 12-17.

Figure 12:
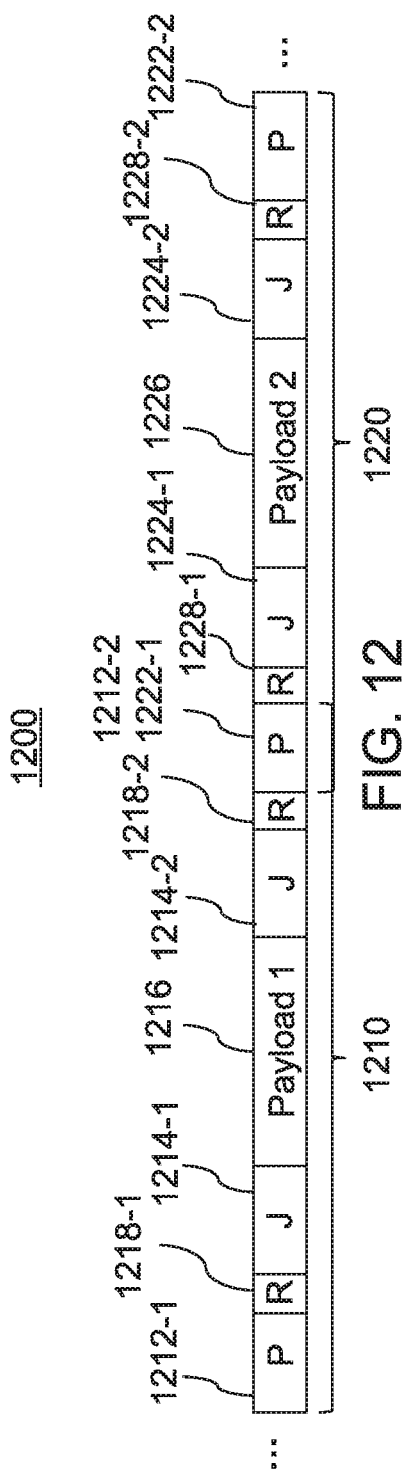
FIG. 12 is a diagram of an exemplary codeword stack strand for golden gate (GG) assembly, in accordance with an embodiment of the present invention.

With reference to FIG. 12, an exemplary codeword stack strand 1200 for GG assembly implementation is provided. The codeword stack strand 1200 includes a plurality of codeword oligonucleotides, including codeword oligonucleotide 1210 and codeword oligonucleotide 1220. Although only two codeword oligonucleotides 1210 and 1220 are shown, the codeword stack strand 1200 can include any number of codeword oligonucleotides. Accordingly, the codework stack strand 1200 depicted in FIG. 12 should not be considered limiting.

Similar to the codeword stack strand 400 described above with reference to FIG. 4, the codeword oligonucleotide 1210 includes a first primer site sequence 1212-1, a first joint site sequence 1214-1, a payload sequence 1216, a second joint site sequence 1214-2 and a second primer site sequence 1212-2, and the codeword oligonucleotide 1220 includes a first primer site sequence 1222-1 (which is the same as the second primer site sequence 1212-2), a first joint site sequence 1224-1, a payload sequence 1326, a second joint site sequence 1224-2 and a second primer site sequence 1222-2. That is, the codeword oligonucleotides 1210 and 1220 each include a payload sequence sandwiched between primer site sequences and joint site sequences.

In contrast to the codework stack strand 400 for PCR assembly implementation described above with reference to FIG. 4, which embeds recognitions sites jointly over the junction of the primer and joint sites, a recognition site (R) for a restriction enzyme has to be independently inserted between each pair of primer and joint sites to implement GG assembly. More specifically, as shown, the codeword oligonucleotide 1210 further includes a first recognition site 1218-1 inserted between primer and joints sites 1212-1 and 1214-1 and a second recognition site 1218-2 inserted between joint and primer sites 1214-2 and 1212-2. Additionally, the codeword oligonucleotide 1220 further includes a first recognition site 1228-1 inserted between primer and joints sites 1222-1 and 1224-1 and a second recognition site 1228-2 inserted between joint and primer sites 1224-2 and 1222-2. Accordingly, the codeword stack strand 1200 includes codewords design for GG assembly.

Each component of the codeword oligonucleotides (e.g., primer site, recognition site, joint site and payload) can have a corresponding base pair (bp) length. For example, each primer site can have, e.g., about 25 bp, each recognition site and joint site can have, e.g., about 6 bp, and each payload can have, e.g., about 20 bp. Regarding design specifications for a codeword oligonucleotide for GG assembly, the codeword oligonucleotide cannot include a home polymer exceeding 3 bp, no recognition site is between each section, and the joint site must not be a palindrome. Accordingly, a codeword stack strand including three codeword oligonucleotides can have a base pair length of, e.g., about 232 bp.

Figure 13:
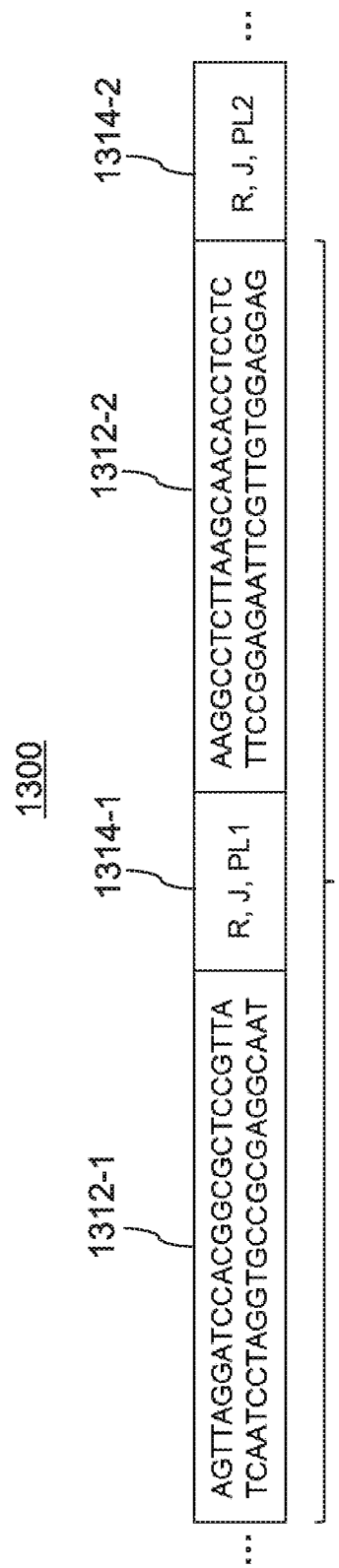
FIG. 13 is another diagram of an exemplary codeword stack strand for GG assembly, in accordance with an embodiment of the present invention.

With reference to FIG. 13, an exemplary codeword stack strand 1300 for GG assembly implementation is provided. As shown, the codework stack strand 1300 includes at least a first codeword oligonucleotide 1310.

The first codeword oligonucleotide 1310 includes a first primer site 1312-1 (e.g., primer site 1212-1 of FIG. 12), a second primer site 1312-2 (e.g., primer site 1212-2/1222-1 of FIG. 12), a first set of nucleic acid sequences 1314-1 including recognition sites, joint sites and a first payload (e.g., components 1214-1, 1214-2, 1216, 1218-1 and 1218-2 of FIG. 12), and a second set of nucleic acid sequences 1314-2 including recognition sites, joint sites and a first payload (e.g., components 1224-1, 1224-2, 1226, 1228-1 and 1228-2 of FIG. 12). In this illustrative embodiment, the first primer site 1312-1 includes a top nucleic acid sequence corresponding to SEQ ID NO:2 and corresponding to a 5' end and a bottom nucleic acid sequence corresponding to SEQ ID NO:3 and corresponding to a 3' end, and the second primer site 1312-2 includes a top nucleic acid sequence corresponding to SEQ ID NO:4 and a bottom nucleic acid sequence corresponding to SEQ ID NO:5.

Components 1312-2 and 1314-2 form a portion of a second codeword oligonucleotide (not labeled). A dial-out of the first codeword oligonucleotide will now be described with reference to FIGS. 14-16.

Figure 14:
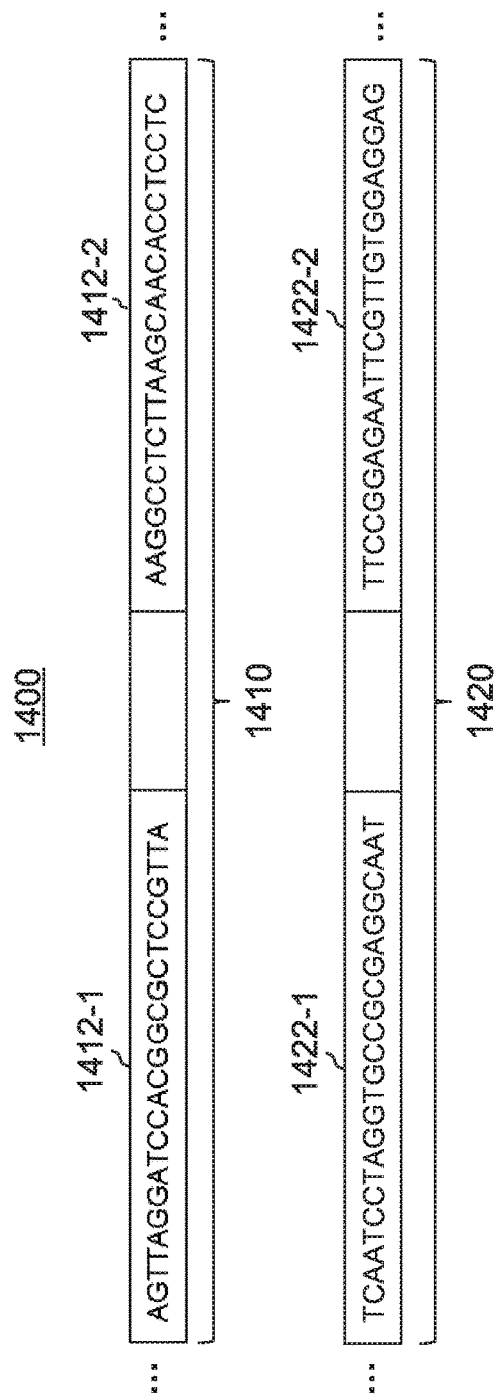
FIG. 14 is a diagram of the denaturing of a codeword oligonucleotide performed for GG assembly, in accordance with an embodiment of the present invention.

With reference to FIG. 14, a diagram 1400 is provided showing the denaturing of the first codeword oligonucleotide 1310 of FIG. 13 into a first sub-strand 1410 and a second sub-strand 1420. The first sub-strand 1410 includes the top nucleic acid sequence of the first primer site 1312-1, denoted as primer portion 1 1412-1, and the top nucleic acid sequence of the second primer site 1312-2, denoted as primer portion 2 1412-2. The second sub-strand 1420 includes the bottom nucleic acid sequence of the first primer site 1312-1, denoted as primer portion 3 1422-1, and the bottom nucleic acid sequence of the second primer site 1312-2, denoted as primer portion 4 1422-2. The denaturing can be performed at any suitable temperature in accordance with the embodiments described herein.

Figure 15:
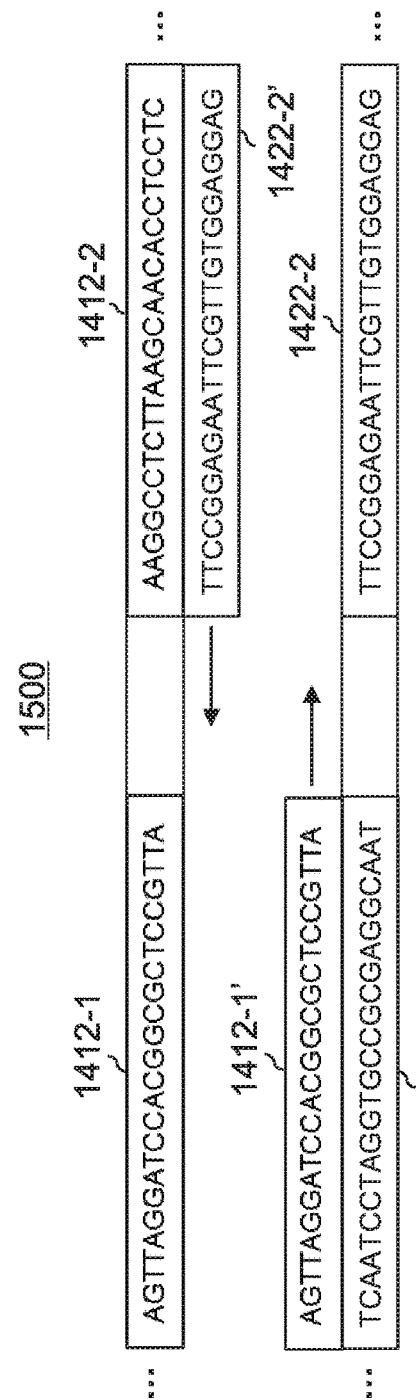
FIG. 15 is a diagram of an annealing step performed for GG assembly using the denatured codeword oligonucleotide, in accordance with an embodiment of the present invention.

With reference to FIG. 15, a diagram 1500 is provided showing an annealing step in which a copy of primer portion 1 1412-1', is paired to complementary primer portion 3 1422-1, and a copy of primer portion 4 1422-2, 1422-2', is paired to complementary primer portion 2 1412-2. Although only one anneal site is shown for each of primer portion copies, there can be multiple anneal sites for one or more of the primer portion copies. The annealing can be performed at any suitable temperature in accordance with the embodiments described herein.

With reference to FIG. 16, a diagram 1600 is provided showing an elongation step to form copies 1610 and 1620 replicating the first codeword oligonucleotide 1310 of FIG. 13. Polymerization can proceed from the 5' direction to the 3' direction from each primer site. Any suitable process can be used to perform the elongation in accordance with the embodiments described herein.

The denaturing, annealing, and elongation steps shown in FIGS. 14-16 can be repeated for a sufficient number of cycles such that the first codeword oligonucleotide 1310 of FIG. 13 becomes a dominant species.

Similar steps can be performed for one or more additional codeword oligonucleotides from the codeword stack strand to be fused with the first codeword oligonucleotide.

Figure 17:
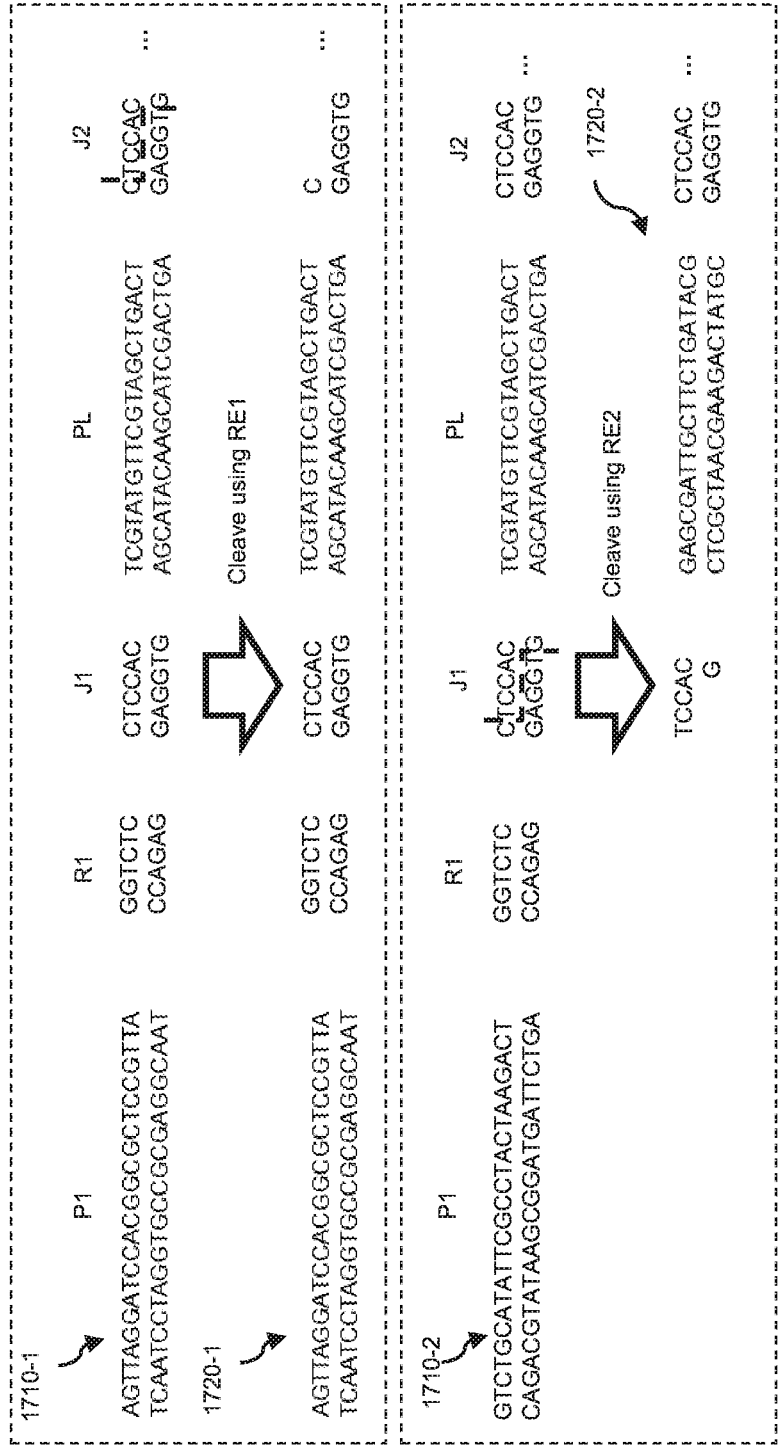
FIG. 17 is a diagram of fusion of codeword oligonucleotides to form a target sequence based on GG assembly, in accordance with an embodiment of the present invention.

For example, with reference to FIG. 17, a diagram 1700 is provided illustrating the fusing of two codeword oligonucleotides. More specifically, a first codeword oligonucleotide 1710-1 and a second codeword oligonucleotide 1710-2 each including a first primer site ("P1"), a first recognition site ("R1"), a first joint site ("J1"), a payload ("PL") and a second joint site ("J2") are shown. The first codeword oligonucleotide 1710-1 is cleaved at J2 using a first restriction enzyme (RE1) to obtain a first cleaved codeword oligonucleotide 1720-1, and the second codeword oligonucleotide 1710-2 is cleaved at J1 using a second restriction enzyme (RE2) to obtain a second cleaved codeword oligonucleotide 1720-2. Any suitable restriction enzymes can be used to first and second codeword oligonucleotides 1710-1 and 1720-2 in accordance with the embodiments described herein.

The first and second codeword oligonucleotides 1710-1 and 1710-2 can then be fused to obtain a fused codeword oligonucleotide 1730. The first and second codeword oligonucleotides 1710-1 and 1710-2 can be fused via an annealing process.

Although only two codeword oligonucleotides are shown fused within the fused codeword oligonucleotide 1730, the processes described above with reference to FIGS. 14-17 can be repeated on additional codeword oligonucleotides to obtain a target sequence of codeword oligonucleotides.

Figure 18:
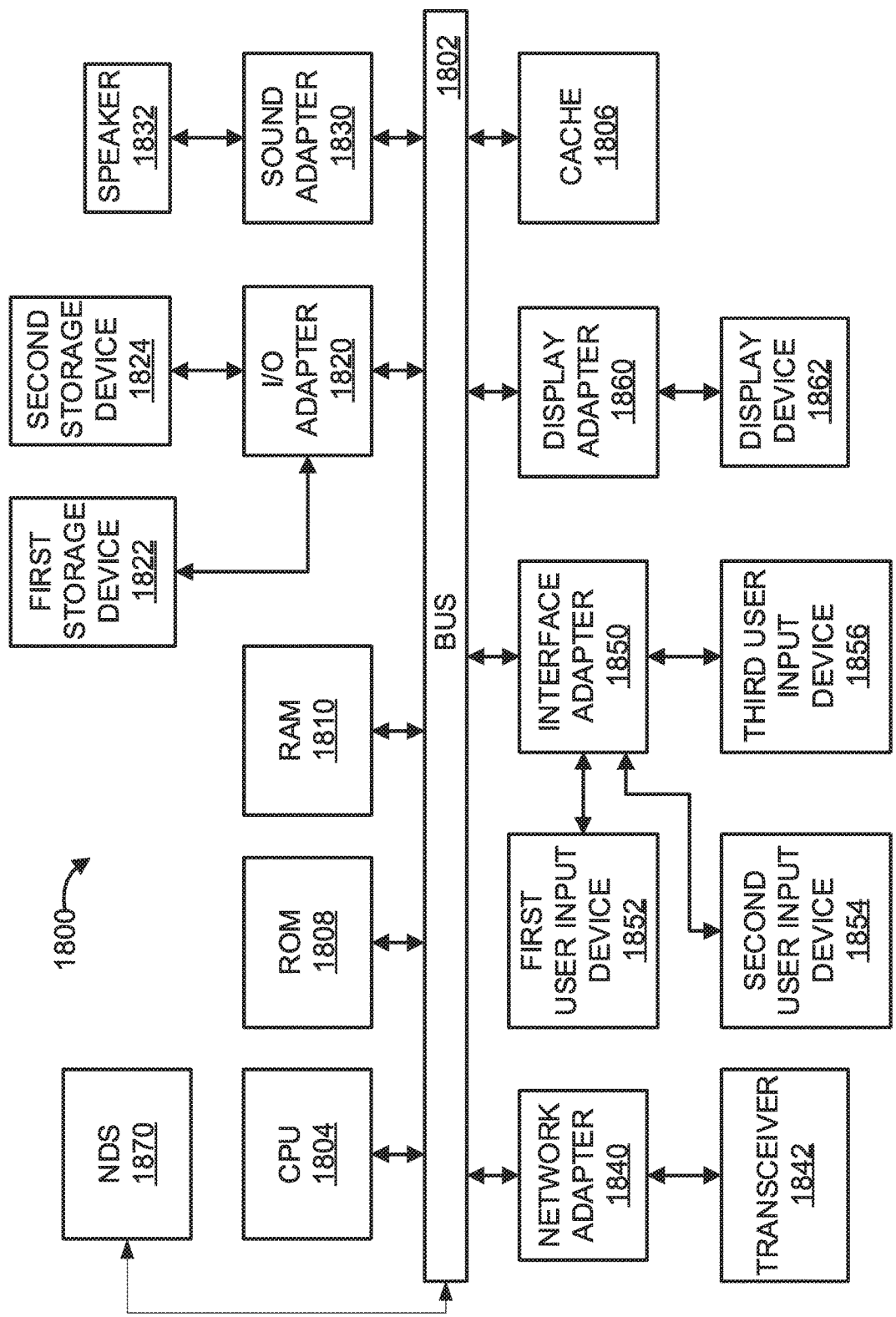
FIG. 18 is a block diagram of a processing system, in accordance with an embodiment of the present invention.

With reference to FIG. 18, an exemplary processing system 1800 to which the present invention may be applied is shown in accordance with one embodiment. The processing system 1800 includes at least one processor (CPU) 1804 operatively coupled to other components via a system bus 1802. A cache 1806, a Read Only Memory (ROM) 1808, a Random Access Memory (RAM) 1810, an input/output (I/O) adapter 1820, a sound adapter 1830, a network adapter 1840, a user interface adapter 1850, and a display adapter 1860, are operatively coupled to the system bus 1802.

A first storage device 1822 and a second storage device 1824 are operatively coupled to system bus 1802 by the I/O adapter 1820. The storage devices 1822 and 1824 can be any of a disk storage device (e.g., a magnetic or optical disk storage device), a solid state magnetic device, and so forth. The storage devices 1822 and 1824 can be the same type of storage device or different types of storage devices.

A speaker 1832 is operatively coupled to system bus 1802 by the sound adapter 1830. A transceiver 1842 is operatively coupled to system bus 1802 by network adapter 1840. A display device 1862 is operatively coupled to system bus 1802 by display adapter 1860.

A first user input device 1852, a second user input device 1854, and a third user input device 1856 are operatively coupled to system bus 1802 by user interface adapter 1850. The user input devices 1852, 1854, and 1856 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 1852, 1854, and 1856 can be the same type of user input device or different types of user input devices. The user input devices 1852, 1854, and 1856 are used to input and output information to and from system 1800.

Nucleic acid data storage (NDS) component 1870 may be operatively coupled to system bus 1802. NDS component 1870 is configured to implement one or more of the functions as described above. NDS component 1870 can be implemented as a standalone special purpose hardware device, or may be implemented as software stored on a storage device. In the embodiment in which NDS component 1870 is software-implemented, although shown as a separate component of the computer system 1800, NDS component 1870 can be stored on, e.g., the first storage device 1822 and/or the second storage device 1824. Alternatively, NDS component 1870 can be stored on a separate storage device (not shown).

Of course, the processing system 1800 may also include other elements (not shown), as readily contemplated by one of skill in the art, as well as omit certain elements. For example, various other input devices and/or output devices can be included in processing system 1800, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 1800 are readily contemplated by one of ordinary skill in the art given the teachings of the present invention provided herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Having described preferred embodiments of systems and methods of efficient assembly of oligonucleotides for nucleic acid based data storage (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claim.

What is claimed is:

1. A system for efficient assembly of oligonucleotides for nucleic acid based data storage, comprising:
   a memory device for storing program code; and
   at least one processor device operatively coupled to the memory device and configured to execute program code stored on the memory device to:
   receive encoded data including binary data encoded into nucleic acid sequence data; and
   assemble a target nucleic acid data strand based on the encoded data by concatenating one or more selected codeword oligonucleotides obtained from a codeword stack strand.

2. The system of claim 1, wherein the binary data is encoded into nucleic acid sequence data using error correction mapping bit pairs to respective nucleobases.

3. The system of claim 1, wherein the at least one processor device is further configured to execute program code stored on the memory device to obtain the codeword stack strand.

4. The system of claim 1, wherein each codeword oligonucleotide of the codeword stack strand includes a payload sequence corresponding to a codeword sandwiched between a pair of primers including a first primer and a second primer and a pair of joint sites.

5. The system of claim 4, wherein the pair of primers includes orthogonal primers.

6. The system of claim 4, wherein the at least one processor device is further configured to assemble the target nucleic acid data strand by:
   selecting a first codeword oligonucleotide for amplification from the codeword stack strand;
   amplifying the first codeword oligonucleotide to generate a set of first codeword oligonucleotides;
   cleaving the first primer from each first codeword oligonucleotide of the set of first codeword oligonucleotides;
   forming a first target sequence based on the set of first codeword oligonucleotides by concatenating a header oligonucleotide with each first codeword oligonucleotide of the set of first codeword oligonucleotides;
   amplifying the first target sequence to generate a set of first target sequences; and
   cleaving the second primer from each first target sequence of the set of target sequences to generate a first subsequence.

7. The system of claim 6, wherein the at least one processor device is further configured to determine that the target nucleic acid data strand has yet to be assembled based on the first subsequence, and select a second codeword oligonucleotide from the codeword stack strand for amplification to assemble the target nucleic acid data strand by concatenating the second codeword oligonucleotide with the first subsequence.

8. A method for efficient assembly of oligonucleotides for nucleic acid based data storage, comprising:
receiving encoded data including binary data encoded into nucleic acid sequence data; and
assembling a target nucleic acid data strand based on the encoded data by concatenating one or more selected codeword oligonucleotides obtained from a codeword stack strand.

9. The method of claim 8, wherein the binary data is encoded into nucleic acid sequence data using error correction mapping bit pairs to respective nucleobases.

10. The method of claim 8, further comprising obtaining the codeword stack strand.

11. The method of claim 8, wherein each codeword oligonucleotide of the codeword stack strand includes a payload sequence corresponding to a codeword sandwiched between a pair of primers including a first primer and a second primer and a pair of joint sites.

12. The method of claim 11, wherein the pair of primers includes orthogonal primers.

13. The method of claim 11, wherein assembling the target nucleic acid data strand further includes:
selecting a first codeword oligonucleotide for amplification from the codeword stack strand;
amplifying the first codeword oligonucleotide to generate a set of first codeword oligonucleotides;
cleaving the first primer from each first codeword oligonucleotide of the set of first codeword oligonucleotides;
forming a first target sequence based on the set of first codeword oligonucleotides by concatenating a header oligonucleotide with each first codeword oligonucleotide of the set of first codeword oligonucleotides;
amplifying the first target sequence to generate a set of first target sequences; and
cleaving the second primer from each first target sequence of the set of target sequences to generate a first subsequence.

14. The method of claim 13, further comprising determining that the target nucleic acid data strand has yet to be assembled based on the first subsequence, and selecting a second codeword oligonucleotide from the codeword stack strand for amplification to assemble the target nucleic acid data strand by concatenating the second codeword oligonucleotide with the first subsequence.

15. A computer program product comprising a non-transitory computer readable storage medium having program instructions embodied therewith, the program instructions executable by a computer to cause the computer to perform a method for efficient assembly of oligonucleotides for nucleic acid based data storage, the method performed by the computer comprising:
receiving encoded data including binary data encoded into nucleic acid sequence data; and
assembling a target nucleic acid data strand based on the encoded data by concatenating one or more selected codeword oligonucleotides obtained from a codeword stack strand.

16. The computer program product of claim 15, wherein the binary data is encoded into nucleic acid sequence data using error correction mapping bit pairs to respective nucleobases.

17. The computer program product of claim 15, wherein the method further includes obtaining the codeword stack strand.

18. The computer program product of claim 15, wherein each codeword oligonucleotide of the codeword stack strand includes a payload sequence corresponding to a codeword sandwiched between a pair of primers including a first primer and a second primer and a pair of joint sites.

19. The computer program product of claim 18, wherein the pair of primers includes orthogonal primers.

20. The computer program product of claim 18, wherein assembling the target nucleic acid data strand further includes:
selecting a first codeword oligonucleotide for amplification from the codeword stack strand;
amplifying the first codeword oligonucleotide to generate a set of first codeword oligonucleotides;
cleaving the first primer from each first codeword oligonucleotide of the set of first codeword oligonucleotides;
forming a first target sequence based on the set of first codeword oligonucleotides by concatenating a header oligonucleotide with each first codeword oligonucleotide of the set of first codeword oligonucleotides;
amplifying the first target sequence to generate a set of first target sequences; and
cleaving the second primer from each first target sequence of the set of target sequences to generate a first subsequence;
determining that the target nucleic acid data strand has yet to be assembled based on the first subsequence; and
selecting a second codeword oligonucleotide from the codeword stack strand for amplification to assemble the target nucleic acid data strand by concatenating the second codeword oligonucleotide with the first subsequence.

* * * * *